United States Patent [19]
Aven et al.

[11] Patent Number: 6,124,301
[45] Date of Patent: Sep. 26, 2000

[54] ENHANCEMENT OF THE EFFICACY OF TRIAZOLOPYRIMIDINES

[75] Inventors: Michael Aven, Mainz, Germany; Henry Van Tuyl Cotter, Trenton, N.J.; Leslie May, Wokingham, United Kingdom

[73] Assignee: American Cyanamid Company, Madison, N.J.

[21] Appl. No.: 09/268,853

[22] Filed: Mar. 15, 1999

Related U.S. Application Data

[60] Provisional application No. 60/078,259, Mar. 17, 1998.

[51] Int. Cl.[7] ............................ A01N 43/00; A01N 43/90; C07D 487/04
[52] U.S. Cl. .......................... 514/258; 514/258; 544/263; 544/118; 544/281
[58] Field of Search .................... 544/263, 218; 514/258

[56] References Cited

U.S. PATENT DOCUMENTS

| | | | |
|---|---|---|---|
| 4,567,263 | 1/1986 | Eichen et al. | 544/263 |
| 4,851,421 | 7/1989 | Iwasaki et al. | 514/352 |
| 5,593,996 | 1/1997 | Pees et al. | 514/258 |
| 5,672,564 | 9/1997 | Wigger et al. | 504/116 |
| 5,817,663 | 10/1998 | Pees et al. | 544/263 |

FOREIGN PATENT DOCUMENTS

| | | | |
|---|---|---|---|
| 0 550 113 | 12/1992 | European Pat. Off. | C07D 487/04 |

OTHER PUBLICATIONS

Stevens, Peter J. G., Organosilicone Surfactants as Adjuvants for Agrochemicals, Mar. 24, 1993, p. 103–122.

*Primary Examiner*—Jose G. Dees
*Assistant Examiner*—Sabiha N. Qazi
*Attorney, Agent, or Firm*—Barbara L. Renda

[57] ABSTRACT

Adjuvants selected from liquid polyalkoxylated aliphatic alcohols, solid sodium hydrocarbyl sulfonates and polyalkoxylated trisiloxanes enhance the efficacy of fungicidal triazolopyrimidines. They can be incorporated into formulations of the fungicidal compounds or be added to spray mixtures (tank mix) as separately formulated additives in order to improve the efficacy, systemicity and spectrum of these fungicides.

13 Claims, No Drawings

ENHANCEMENT OF THE EFFICACY OF TRIAZOLOPYRIMIDINES

This application claims benefit of provisional appln No. 60/078,259 filed Mar. 17, 1998.

BACKGROUND OF THE INVENTION

This invention concerns the enhancement of the efficacy of fungicidal triazolopyrimidines by addition of certain adjuvants, preparations through which this effect can be exploited, as well as the use of combinations of fungicidal triazolopyrimidines and these adjuvants in the control of phytopathogenic fungi.

As a rule, inert carrier ingredients must be used to bring crop protection agents, for example, fungicidal compounds, into a form that the user can apply them either as such, or after dilution with water. The choice of formulation type and inert ingredients for that formulation type such as carrier ingredients often determines to a significant extent whether the active ingredient can display its full efficacy on application.

The efficacy of the active components can often be improved by addition of other (active) ingredients. The observed efficacy of the combination of ingredients can sometimes be significantly higher than that would be expected from the amounts of the individual ingredients used, thus indicating synergism from the components of the combination.

The usual components of formulations such as carriers and inert ingredients (e.g. organic solvents, suspension agents, emulsifiers, wetting agents, solubilizing agents) which do not themselves possess pesticidal activity, however, do not usually lead to an unexpected increase in efficacy.

International Patent Application WO 95/01722 discloses pesticidal formulations containing non-ionic surface-active agents which can be selected, inter alia, from liquid polyalkoxylated aliphatic alcohols. However, the addition of these agents is directed to improving the storage stability of the formulations, and there is no report of enhancing the activity of fungicides used in the formulations.

U.S. Pat. No. 4,851,421 discloses the use of polyalkylene-type nonionic surface active agents derived from the alkoxylation of fatty alcohols with alkyleneoxides, polyoxyalkylene mono- or dialkylphenylether or polyoxyalkylene sorbitan fatty acid esters.

EP 0 071 792-A, EP 0 550 113-A, WO 98/46607 and WO 98/46608 disclose fungicidal triazolopyrimidine compounds. Although these compounds are effective fungicides when applied to plants in conventional formulations, it is economically and environmentally desirable to provide a means to lower the dose required for effective disease control.

SUMMARY OF THE INVENTION

The present invention relates to a method for the enhancement of the activity and/or systemicity of fungicidal compositions for application on plants containing at least one triazolopyrimidine of formula I

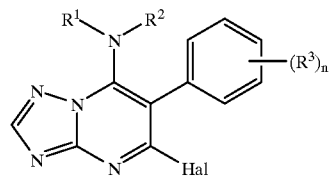

wherein $R^1$ and $R^2$ each independently represent hydrogen, or an optionally substituted alkyl, alkenyl, alkynyl, alkadienyl, haloalkyl, aryl, heteroaryl, cycloalkyl, bicycloalkyl or heterocyclyl group, or $R^1$ and $R^2$, together with the adjacent nitrogen atom represent an optionally substituted heterocyclic ring, $R^3$ represents a halogen atom or an alkyl or alkoxy group, n represents an integer from 0 to 5, and Hal represents a halogen atom, which comprises the addition of an adjuvant selected from the group consisting of
  (a) non-ionic surface-active agents selected from liquid polyalkoxylated aliphatic alcohols and polyalkoxylated plant oils;
  (b) solid sodium hydrocarbyl sulfonates; and
  (c) polyalkoxylated trisiloxanes, to the formulation or the tank mix containing the triazolopyrimidine of formula I.

Most surprisingly, the compositions used according to the present invention also expand the efficacy profile of the triazolopyrimidines of formula I, since these compositions can be successfully applied in normal application amounts to control fungal diseases of plants which they had previously required uneconomically high doses of the triazolopyrimidines of formula I.

These and other objects and features of the invention will become more apparent from the detailed description set forth hereinbelow.

DETAILED DESCRIPTION OF THE PREFERRED EMBODIMENTS

It has now been found that amounts of fungicidal triazolopyrimidines of formula I which must be applied to plants can be lowered considerably, with respect to the amounts usually required to achieve the same fungicidal effect, if these fungicidal compounds or their formulations are applied in combination with one or more adjuvants selected from the group consisting of
  (a) non-ionic surface-active agents selected from liquid polyalkoxylated aliphatic alcohols and polyalkoxylated plant oils;
  (b) solid sodium hydrocarbyl sulfonates; and
  (c) polyalkoxylated trisiloxanes.

The term "plants" as used hereinabove and hereinbelow includes all kinds of plants and all plant parts, in particular, foliage, roots, fruits and seeds.

The biological activity of the active ingredient of formula I can be increased by including any of these adjuvants in the spray dilution or directly in the formulation. An "adjuvant" is defined here as a substance which can increase the biological activity of an active ingredient but is not itself significantly biologically active.

The adjuvants (a), i.e. the liquid polyalkoxylated aliphatic alcohols and polyalkoxylated plant, oils are particularly useful in liquid formulations, in particular, in suspension concentrates (SC) and in emulsifiable concentrates (EC).

The polyalkoxylated aliphatic alcohols are obtainable by alkoxylation of fatty alcohols having 9–24, preferably 12–22 and in particular, 14–20 carbon atoms, with alkyleneoxide having 2–6, preferably 2–3 carbon atoms, in particular, with a mixture of ethyleneoxide and propyleneoxide. The aliphatic moieties of the said fatty alcohols may be straight-chain or branched.

Particularly preferred are polyalkoxylated alcohols which are straight-chained or branched aliphatic $C_{9-20}$ alcohols alkoxylated with 2 to 15 $C_{2-6}$ alkoxy groups.

Of particular interest are those polyalkoxylated aliphatic alcohols, which are liquids at temperatures below 20° C. having a viscosity of 30 to 100, in particular 50 to 80 mPa.s at 25° C. The compounds which are commercially available under the trademark Plurafac® LF (Tensid-Chemie, Köln/BASF AG, Ludwigshafen), in particular Plurafac® LF 224, Plurafac® LF 403, Plurafac® LF 700 and Plurafac® LF 1300 have been found to be especially advantageous in the methods of the present invention.

The Plurafac® LF surfactants are characterized by the first number after the "LF" as indicating the number of moles of the higher alkylene oxide (e.g., propylene oxide, butylene oxide) contained on average in the alkylene oxide chain per mole of alcohol. For example, Plurafac® LF 700 contains 7 higher alkylene oxide units per alkylene oxide chain.

Further preferred alcohol alkoxylates are the mono-branched alcohol alkoxylates such as Atplus® MBA 1303 (branched alcohol alkoxylate with ethoxy and propoxy units) of Uniqema (formerly ICI Surfactant).

Preferred polyalkoxylated plant oils are, as a rule, obtainable by alkoxylation of triglycerides. The alkoxylation of triglycerides results in mixtures of compounds with one to three glyceride side chains having 9–24, preferably 12–22 and, in particular, 14–20 C-atoms, in particular, with ethyleneoxide. Preferably these compounds correspond to mixed oligomers resulting from the alkoxylation of castor or canola oil. Most preferred are castor and canola oil ethoxylate having 20 to 50, in particular 30 to 40 ethyleneoxide units, which are commercially available under the tradename Eumulgin®, in particular, Eumulgin® CO 3522 (Henkel KGaA) or Ukanil®, in particular, Ukanil® 2507 (Uniqema).

The adjuvants which are solid sodium hydrocarbyl sulfonates are in particular useful for solid formulations, in particular, wettable powders (WP) or water dispersable granulates (WG). These adjuvants are, as a rule, sulfonates of linear fatty alcohols having 9–20, preferably 12–18 and, in particular 14–16, carbon atoms. The aliphatic moieties of the the fatty alcohols may be straight-chain, branched, saturated or unsaturated. Particularly preferred are linear, unsaturated fatty alcohols such as sodium $C_{9-20}$ olefin sulfonates. Witconate® AOK, commercially available from Witco Corporation, Houston, has been proven to be especially advantageous in the methods of this invention.

The adjuvants which are polyalkoxylated trisiloxanes are, as a rule, polyalkoxylated heptaalkyl trisiloxanes, in particular alpha-1,1,1,3,5,5,5-heptamethyltrisioxanylpropyl-omega-hydroxy or -omega-alkoxy compounds. The compounds commercially available under the trademark Silwet® (OSi Specialities Germany GmbH, Düsseldorf), in particular Silwet® L77 and Silwet® 408, have been proven to be especially advantageous in the methods of this invention.

The enhancement in efficacy by addition of the adjuvants is observed for the fungicidal triazolopyrimidines of formula 1, preferably, those compounds of formula I wherein $R^1$ and $R^2$ together with the adjacent nitrogen atom represent an optionally substituted 6-membered heterocyclic ring, or wherein $R^1$ represents a $C_{1-6}$ alkyl, a $C_{1-6}$ haloalkyl, in particular, $C_{1-6}$ fluoroalkyl, most preferably a 1,1,1-trifluoroprop-2-yl group, or a $C_{3-8}$ cycloalkyl group and $R^2$ represents a hydrogen atom or a $C_{1-6}$ alkyl group and/or wherein

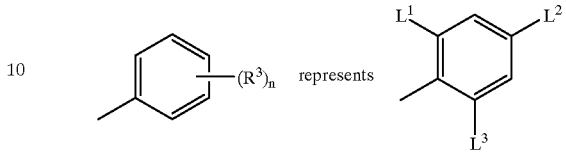

wherein $L^1$ represents a halogen atom, preferably fluorine or chlorine and $L^2$ and $L^3$ each independently represent a hydrogen atom or a halogen atom, preferably fluorine and/or wherein Hal represents a chlorine atom.

In a particularly preferred embodiment, the triazolopyrimidine is selected from 5-chloro-6-(2-chloro-6-fluorophenyl)-7-N-(4-methylpiperid-1-yl)-[1,2,4]triazolo[1,5-a]pyrimidine, (also referred to herein as compound IA) and 5-chloro-6-(2,4,6-trifluorophenyl)-7-(1,1,1-trifluoroprop-2-ylamino)-[1,2,4]triazolo[1,5-a]pyrimidine, (also referred to herein as compound IB).

The fungicidal compositions of this invention can comprise other compounds having biological activity in addition to the triazolopyrimidine of formula I, e.g. compounds having similar or complementary fungicidal activity or compounds having plant growth regulating, herbicidal or insecticidal activity.

The other fungicidal compounds can be, for example, those which is capable of combating diseases of cereals (e.g. wheat) such as those caused by Erysiphe, Puccinia, Septoria, Gibberella and Helminthosporium spp., seed and soil borne diseases, downy and powdery mildews on vines, and powdery mildew and scab on apples, Bortrytis diseases on numerous crops and Cercospora diseases on numerous crops, rice blast and rice sheath blight. These mixtures of fungicides can have a broader spectrum of activity than the compound of general formula I alone.

Examples of the other fungicidal compounds are AC 382042, alanycarb, aldimorph, ampropylfos, andoprim, anilazine, azaconazole, azafenidin, azoxystrobin, benalaxyl, benodanil, benomyl, benzamacril, bialaphos, biloxazol, binapacryl, biphenyl, bitertanol, blasticidin S, Bordeaux mixture, bromuconazole, bupirimate, butenachlor, buthiobate, captafol, captan, carbendazim, carboxin, carpropamid, carvone, chinomethionate, chlorbenzthiazon, chlorfenazol, chloroneb, chloropicrin, chlorothalonil, chlozolinate, clozylacon, copper-containing compounds such as copper oxychloride, and copper sulfate, cufraneb, cycloheximide, cymoxanil, cypofuram, cyproconazole, cyprodinil, cyprofuram, debacarb, dichlofluanid, dichlone, dichloran, dichlorophen, diclobutrazol, diclocymet, diclomezine, dicloran, diethofencarb, difenoconazole, difenzoquat, diflumetorim, dimefluazole, dimethirimol, dimethomorph, diniconazole, dinocap, diphenylamin, dipyrithione, ditalimfos, dithianon, dodemorph, dodine, drazoxolon, edifenphos, epoxiconazole, etaconazole, ethirimol, ethoxyquin, etridiazole, famoxadone, fenapanil, fenamidone, fenaminosulph, fenarimol, fenbuconazole, fenfuram, fenhexamid, fenitropan, fenpiclonil, fenpropidin, fenpropimorph, fentin, fentin acetate, fentin hydroxide, ferbam, ferimzone, fluazinam, fludioxonil, flumetover, fluoromid, fluquinconazole, flurprimidol, flusilazole, flusulfamide, flutolanil, flutriafol, folpet, fosetyl-aluminium, fuberidazole, furalaxyl, furametpyr, furcarbonil, furconazole-cis, furmecyclox, guazatine, hexachlorobenzol, hexaconazole, hydroxyisoxazole, hymexazole, IKF-916, imazalil, imibenconazole, iminoctadine, iodocarb, ipconazole, iprobenfos, iprodione, iprovalicarb, isoprothiolane, isovaledione, kasugamycin, RH-7281, kitazin P, kresoxim-methyl, mancozeb, maneb, mefenoxam, meferimzone, mepanipyrim, mepronil, metalaxyl, metconazole, methasulfocarb, methfuroxam, metiram, metomeclam, metominostrobon, metsulfovax, MON 65500, myclobutanil, myclozolin, neoasozin, nickel dimethyldithiocarbamate, nitrothalisopropyl, nuarimol, ofurace, organo mercury compounds, oxadixyl, oxamocarb, oxasulfuron, oxycarboxin, paclobutrazol, pefurazoate, penconazole, pencycuron, phenazineoxide, phosdiphen, phthalide, pimaricin, piperalin, polyoxin D, polyram, probenazole, prochloraz, procymidone, propamocarb, propiconazole, propineb, prothiocarb, pyracarbolid, pyrazophos, pyrifenox, pyrimethanil, pyroquilon, pyroxyfur, quinconazole, quinomethionate, quinoxyfen, quintozene, rabenazole, spiroxamine, SSF-126, SSF-129, streptomycin, sulfur, tebuconazole, tecloftalame, tecnazene, tetcyclacis, tetraconazole, thiabendazole, thicyofen, thifluzamide, thiophanate-methyl, thiram, tioxymid, tolclofosmethyl, tolylfluanid, triadimefon, triadimenol, triazbutil, triazoxide, trichlamid, tricyclazole, tridemorph, trifloxystrobin, triflumizole, triforine, triticonazole, uniconazol, validamycin A, vapam, vinclozolin, XRD-563, zarilamid, zineb, ziram.

In addition, the compositions according to the invention may contain at least one compound of formula I and any of the following classes of biological control agents such as viruses, bacteria, nematodes, fungi, and other microorganism which are suitable to control insects, weeds or plant diseases or to induce host resistance in the plants. Examples of such biological control agents are: *Bacillus thuringiensis, Vefficillium lecanii, Autographica califomica NPV, Beauvaria bassiana, Ampelomyces quisqualis, Bacilis subtilis, Pseudomonas cholororaphis, Pseudomonas fluorescens, Steptomyces griseoviridis* and *Trichoderma harianum*.

Moreover, the compositions according to the invention may contain at least one compound of formula I and a chemical agent that induces the systemic acquired resistance in plants such as, for example, nicotinic acid or derivatives thereof, 2,2-dichloro-3,3-dimethylcyclopropylcarboxylic acid or BION.

The adjuvants which are usable according to the invention can be included in the formulation or can be added in a suitable form during the preparation of the spray mix (tank-mix). In latter case, they are added preferably as a separate preparation, optionally with other additives, or in a mixture with a dispersing agent and/or, where desirable, with further adjuvants so as to ensure that they are homogenously dispersed in the spray mix.

Therefore, the present invention relates to fungicidal formulations comprising at least one compound of formula I, and one or more adjuvants selected from the group:
  (a) non-ionic surface-active agents selected from liquid polyalkoxylated aliphatic alcohols and polyalkoxylated plant oils;
  (b) solid sodium hydrocarbyl sulfonates; and
  (c) polyalkoxylated trisiloxanes.

The fungicidal compounds can be applied as conventional formulations which can, but do not necessarily have to, contain adjuvants according to the invention, and where desirable, contain additional ingredients such as antioxidants and emulsifiers.

The appropriate relative amounts of active ingredient of formula I and the adjuvant (a), (b) and/or (c) are, in accordance with the invention, between 100:75 and 100:100,000, preferably between 100:90 and 100:50,000 and, in particular, between 100:125 and 1:5,000. In general, and within certain limits, the fungicidal efficacy is enhanced to a higher degree by the addition of larger amounts of the adjuvant (a), (b) or (c) as is shown in the experimental results described below.

In a preferred embodiment, the adjuvant is added to the tank mix together with a the triazolopyrimidine of formula I.

Therefore, the present invention relates also to a kit for the preparation of a spray mixture consisting of two separate containers:
  a first container containing a composition which comprises at least one fungicide of formula I, optionally with conventional inert ingredients and carriers;
  a second container containing a composition which comprises at least one compound selected from the group consisting of:
    (a) non-ionic surface-active agents selected from liquid polyalkoxylated aliphatic alcohols and polyalkoxylated plant oils;
    (b) solid sodium hydrocarbyl sulfonates; and
    (c) polyalkoxylated trisiloxanes.

In a preferred embodiment, the kit will consist of two containers, each with dispensing means to allow the easy and correct addition of the active ingredient (a) and the additive (b) to the tank mix.

Recommended doses for various applications in the absence of an adjuvant are known for the fungicidal compounds of formula I. The efficacy thereof can be enhanced in accordance with the invention. For instance, addition of the adjuvants suggested here can (depending on the active ingredient, the adjuvant and their respective amounts) reduce the amount of active ingredient per hectare required in these recommendations by half or more, so that additional diseases can be controlled at reasonable doses of the compound of formula I.

In a preferred embodiment, the adjuvants (a), (b) or (c) in combination with the fungicide of formula I are applied at rates of 100 to 3000 mL/ha, preferably 200 to 2000 mL/ha, in particular, 225 to 1400 mL/ha.

An important advantage of the present invention is the rapid onset and the high persistency of activity afforded by the compositions of the invention. This enlarges the period for application of the fungicide and makes its use more flexible.

The fungicidal formulations can according to the present invention be used in combination with said adjuvants to increase both prophylactic and curative control.

The adjuvants according to the invention, the compounds of formula I, and usual inert ingredients and carriers can be processed to produce liquid or solid formulations known in the art, as for example solutions, emulsions, WPs (wettable powders), WGs (water-dispersible granules), SCs (suspension concentrates), ECs (emulsifiable concentrates), low volume or ultra low volume preparations and granules.

The preparations usually contain liquid and/or solid carriers or solubilizing agents such as organic solvents like ketones, alcohols, fluid aliphatic, araliphatic or aromatic compounds, fine natural or synthetic silicates or carbonates ionic and/or non-ionic surfactants which function as emulsifiers, dispersing agents or wetting agents. Antifoams, preservatives, structure agents and antifreeze agents may be added. Suitable additives and carrier substances are described in the literature and are well known to the skilled artisan.

A formulation according to the invention preferably contains from 0.5% to 95% by weight (w/w) of the active compound of formula I and an adjuvant selected from the group consisting of
  (a) non-ionic surface-active agents selected from liquid polyalkoxylated aliphatic alcohols;
  (b) solid sodium hydrocarbyl sulfonates; and
  (c) polyalkoxylated trisiloxanes, A carrier in the composition of the invention is any material with which the active ingredient is formulated to facilitate application to the locus to be treated. This may be, for example, a plant, seed or soil, or to facilitate storage, transport or handling. A carrier may be a solid or a liquid, including material which is normally a gas but which has been compressed to form a liquid.

The compositions may be manufactured into emulsifiable concentrates, solutions, oil-in-water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances such as fillers, solvents, solid carriers, surface active compounds (surfactants), and optionally, solid and/or liquid additives. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. amyl alcohol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, are those such as mineral fillers such as calcite, talc, kaolin, montmorillonite or attapulgite. Optionally, the physical properties may be improved by addition of highly dispersed silica gel or polymers. Carriers for granules are those such as porous material, e.g. pumice, kaolin, sepiolite, bentonite; non-sorptive carriers are those such as calcite or sand. Additionally, pre-granulated inorganic or organic materials of many types can be used, such as dolomite or crushed plant residues.

Fungicidal compositions are usually formulated and transported in a concentrated form which is subsequently diluted by the user before application. The presence of small amounts of a carrier which is a surfactant facilitates this process of dilution. Thus, preferably at least one carrier in a formulation of the invention is a surfactant. For example, the formulation may contain at two or more carriers at least one of which is a surfactant.

Surfactants may be nonionic, anionic, cationic or zwifterionic substances with good dispersing, emulsifying and wetting properties depending on the nature of the compound according to general formula I to be formulated. Surfactants may also include mixtures of individual surfactants.

The compositions of the invention may be, for example, formulated as wettable powders, water dispersible granules, dusts, granules, solutions, emulsifiable concentrates, emulsions, suspension concentrates and aerosols. Wettable powders (WP) usually contain 5 to 90% w/w of the active ingredients and usually contain, in addition to solid inert carrier, 3 to 10% w/w of dispersing and wetting agents and, where necessary, 0 to 10% w/w of stabilizer(s) and/or other additives such as antifoams. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules (WG) and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small water dispersible granules. Emulsifiable concentrates (EC) usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates (SC) are usually milled so as to obtain a stable, non-sedimenting flowable product and usually contain 5 to 75% w/v active ingredient, 0.5 to 15% w/v of dispersing agents, 0.1 to 10% w/v of structure agents, such as protective colloids and thixotropic agents, 0 to 10% w/v of other additives, such as defoamers, corrosion inhibitors, stabilizers and antifreeze agents. The continuous phase of an SC consists as a rule of water or an organic liquid, in which the active ingredient is substantially insoluble. Certain organic solids or inorganic salts may be present dissolved in the formulation to assist in preventing sedimentation and crystalization or as antifreeze agents for water.

Aqueous solutions, dispersions and emulsions, for example, compositions obtained by diluting the formulated product according to the invention with water, also lie within the scope of the invention.

As a commodity, the formulations are preferably packaged in a concentrated form whereas the end user generally employs diluted compositions. The compositions may be diluted to a concentration down to 0.001% of active ingredient. The doses usually are in the range from 0.01 to 10 kg a.i./ha.

The following examples of formulations according to the invention (formulations A to I) are presented to illustrate, but not to restrict, this invention:

Ingredients Used in Examples

| Trade Name | Chemical Identity |
| --- | --- |
| Atplus ® MBA 1303 | monobranched polyalkoxylated aliphatic alcohol |
| Eumulgin ® CO 3522 | canola oil ethoxylate |
| Plurafac ® LF700 | liquid polyalkoxylated aliphatic alcohol |
| Silwet ® 408 | polyalkoxylated trisiloxane |
| Silwet ® L77 | polyalkoxylated trisiloxane |
| Ukanil ® 2507 | castor oil ethoxylate |
| Witconate ® AOK | solid sodium hydrocarbyl sulfonate |
| Atlox ® 4856B | mixture of calcium alkyl aryl sulfonate, fatty alcohol ethoxylates and light aromatics |
| Atlox ® 4885 | sodium trioleate, technical grade |
| Borresperse ® NH | ammonium lignosulfonate |
| Hypermer ® LP5 | quaternary ammonium derivative of polycondensed fatty acid |
| Lutensol ® TO12 | ethoxylated iso-tridecanol |
| Morwet ® D-425 | alkylnaphthalene sulfonic-acid formaldehyde condensate |

-continued

Ingredients Used in Examples

| Trade Name | Chemical Identity |
|---|---|
| Nekal ® BX trocken | sodium alkylnaphthalene sulfonate |
| Pluronic ® PE 10500 | ethyleneoxide/propyleneoxide copolymer with about 50% of polyethylene glycol |
| Proxel ® GXL | aqueous dipropylene glycol solution containing 20% 1,2-benisothiazolin-3-one |
| Rhodopol ® 23 | heteropolysaccharide having a molecular weight of about 2,000,000 g/mol |
| Rhodorsil ® 426 R | nonionic aqueous emulsion of poly-dimethylsiloxanes |
| Shellsol ® A | mixture of $C_9$–$C_{10}$ aromatic hydrocarbons |
| Solvesso 200 | mixture of alkylbenzenes |
| Soprophor ® FL | polyoxyethylene polyaryl phenyl ether phosphate amine salt |
| Tensiofix ® BCZ | sodium alkyl sulfate |
| Tensiofix ® LX Special | lignosulfonate |

Formulation A: Suspoemulsion (SE)

| Component | Amount [g/L] | Ingredient |
|---|---|---|
| active ingredient | 100.0 | Compound IA |
| adjuvant | 200.0 | Plurafac ® LF700[2] |
| dispersant | 25.0 | Morwet ® D-425[1] |
| dispersant | 5.0 | Pluronic ® PE 10500[2] |
| antifoam agent | 2.0 | Rhodorsil ® 426 R[3] |
| preservative | 1.0 | Proxel ® GXL[4] |
| structure agent | 2.5 | Rhodopol ® 23[3] |
| antifreeze agent | 30.0 | propylene glycol |
| solvent | 200.0 | Shellsol ® A[5] |

[1]Witco Corporation, Houston, Texas
[2]Tensid-Chemie, Köln/BASF AG, Ludwigshafen
[3]Rhodia, formerly Rhône-Poulenc GmbH, Frankfurt
[4]Zeneca GmbH, Frankfurt
[5]Shell AG Formulation B: Suspension concentrate (SC)

| Component | Amount [g/L] | Ingredient |
|---|---|---|
| active ingredient | 100.0 | Compound IA |
| dispersant | 25.0 | Morwet ® D-425[1] |
| dispersant | 5.0 | Pluronic ® PE10500[2] |
| antifoam agent | 2.0 | Rhodorsil ® 426 R[3] |
| preservative | 1.0 | Proxel ® GXL[4] |
| structure agent | 2.0 | Rhodopol ® 23[3] |
| antifreeze agent | 50.0 | propylene glycol |
| water | to 100 mL | |

[1]Witco Corporation, Houston, Texas
[2]Tensid-Chemie, Köln/BASF AG, Ludwigshafen
[3]Rhodia, formerly Rhône-Poulenc GmbH, Frankfurt
[4]Zeneca GmbH, Frankfurt The SC Formulation B described above is mixed before application with water to give a spray mix with the desired concentration of active ingredient. As the adjuvant, one or more non-ionic surface-active agents selected from liquid polyalkoxylated aliphatic alcohols, in particular, Plurafac® LF700, are added to the resulting tank mix at a level of 50–10,000 g and preferably 250–1000 g, per 1 liter formulation, or one or more polyalkoxylated trisiloxanes, in particular Silwet® 408 or Silwet® L77 are added at a level of 50 to 5,000 g per 1 liter formulation.

Formulation C: Suspension concentrate (SC)

| Component | Amount [g/L] | Ingredient |
|---|---|---|
| active ingredient | 100.0 | Compound IA |
| antifreeze agent | 80.0 | propylene glycol |
| dispersant | 30.0 | Soprophor ® FL[3] |
| antifoam agent | 1.5 | Rhodorsil ® 426 R[3] |
| preservative | 1.5 | Proxel ® GXL[4] |
| structure agent | 2.0 | Rhodopol ® 23[3] |
| water | to 1000 mL | |

[3]Rhodia, formerly Rhône-Poulenc GmbH, Frankfurt
[4]Zeneca GmbH, Frankfurt

The SC Formulation C described above is mixed before application with water to give a spray mix with the desired concentration of active ingredient. As the adjuvant, a non-ionic surface-active agent selected from liquid polyalkoxylated aliphatic alcohols, in particular, Plurafac® LF700, is added to the resulting tank mix at a level of 50–10,000 g, and preferably 250–1000 g, per 1 liter of formulation.

Formulation D: Suspension concentrate (SC)

| Component | Amount [g/L] | Ingredient |
|---|---|---|
| active ingredient | 100.0 | Compound IA |
| Adjuvant | 300.0 | Plurafac ® LF700[2] |
| Dispersant | 10.0 | Hypermer LP5[6] |
| Dispersant | 50.0 | Atlox 4856B[6] |
| Dispersant | 50.0 | Atlox 4885[6] |
| Solvent | to 1000 mL | Solvesso 200[7] |

[2]Tensid-Chemie, Köln/BASF AG, Ludwigshafen
[6]Uniqema, Everberg
[7]Deutsche Exxon, Cologne Formulation E: Water-dispersible granules (WG)

| Component | Amount [g/kg] | Ingredient |
|---|---|---|
| active ingredient | 100.0 | Compound IA |
| disintegrant | 50.0 | Ammonium sulfate |
| dispersant | 80.0 | Borresperse ® NH[8] |
| wetting agent | 20.0 | Nekal ® BX trocken[2] |
| filler | 750.0 | kaolin |

[2]Tensid-Chemie, Köln/BASF AG, Ludwigshafen
[8]Borregaard Industries Ltd., Sarpsborg The WG formulation E described above is mixed before application with water to give a spray mix with the desired concentration of active ingredient. As the adjuvant, one or more solid sodium hydrocarbyl sulfonates, in particular, Witconate® AOK, are added to the resulting tank mix at a level of 50–10,000 g, and preferably 250–1000 g, per 1 kg of formulation.

Formulation F: Water dispersible granules (WG)

| Component | Amount [g/kg] | Ingredient |
|---|---|---|
| active ingredient | 275.0 | Compound IA |
| adjuvant | 550.0 | Witconate ® AOK[1] |

-continued

| Component | Amount [g/kg] | Ingredient |
|---|---|---|
| dispersant | 100.0 | Tensiofix ® LX Special[9] |
| wetting agent | 75.0 | Tensiofix ® BCZ[9] |

[1] Witco Corporation, Houston, Texas
[9] Omnichem S.A., Louvain-La-Neuve

Formulation G: Wettable Powder (WP)

| Component | Amount [g/kg] | Ingredient |
|---|---|---|
| active ingredient | 200.0 | Compound IA |
| dispersant | 90.0 | Tensiofix ® LX Special[9] |
| wetting agent | 30.0 | Tensiofix ® BCZ[9] |
| filler | 680.0 | Kaolin |

[9] Omnichem S.A., Louvain-La-Neuve

The WP formulation G described above is mixed before application with water to give a spray mix with the desired concentration of active ingredient. As the adjuvant, one or more solid sodium hydrocarbyl sulfonates, in particular, Witconate® AOK, are added to the resulting tank mix at a level of 50–10,000 g, and preferably 250–1000 g, per 1 kg of formulation.

Formulation H: Dispersible concentrate (DC)

| Component | Amount [g/L] | Ingredient |
|---|---|---|
| active ingredient | 100.0 | Formula IA |
| dispersant | 50.0 | Pluronic ® PE 10500[2] |
| dispersant | 50.0 | Lutensol ® TO12[2] |
| solvent | to 1000 mL | benzyl alcohol |

[2] Tensid-Chemie, Köln/BASF AG, Ludwigshafen

The DC formulation H described above is mixed for use with water to give a spray mix with the desired concentration of active ingredient. As adjuvant, one or more non-ionic surface-active agent selected from liquid polyalkoxylated aliphatic alcohols, in particular, Plurafac® LF700, or one or more polyalkoxylated trisiloxane, in particular, Silwet® L77 or Silwet® 408, are added to the resulting tank mix at a level of 50–1000 ppm, and preferably 250–1000 ppm.

Formulation I: Suspension concentrate (SC)

| Component | Amount [g/L] | Ingredient |
|---|---|---|
| active ingredient | 100.0 | Compound IB |
| dispersant | 25.0 | Morwet ® D-425[1] |
| dispersant | 5.0 | Pluronic ® PE 10500[2] |
| antifoam agent | 2.0 | Rhodorsil ® 426 R[3] |
| preservative | 2.0 | Proxel ® GXL[4] |
| structure agent | 3.0 | Rhodopol ® 23[3] |
| antifreeze agent | 50.0 | propylene glycol |
| water | to 1000 mL | |

[1] Witco Corporation, Houston Texas
[2] Tensid-Chemie, Köln/BASF AG, Ludwigshafen
[3] Rhodia, formerly Rhône-Poulenc GmbH, Frankfurt
[4] Zeneca GmbH, Frankfurt.

The SC formulation I described above is mixed before application with water to give a spray mix with the desired concentration of active ingredient. As the adjuvant, one or more non-ionic surface-active agent selected from liquid polyalkoxylated aliphatic alcohols or polyalkoxylated plant oils, in particular, Plurafac® LF700, Atplus® MBA 1303, Eumulgin® CO 3522 or Ukanil® 2507, are added to the resulting tank mix at a level of 50–10,000 g and preferably 250–1000 g per 1 liter formulation.

It is also an object of the invention to provide a method for the control of phytopathogenic fungi, characterized by the use of the compounds of formula I, in particular formula IA in combination with one or more adjuvants selected from the group consisting of:

(a) non-ionic surface-active agents selected from liquid polyalkoxylated aliphatic alcohols;

(b) solid sodium hydrocarbyl sulfonates; and (c) polyalkoxylated trisiloxanes,

Examples of plant diseases that can be combated with the fungicidal formulations according to the present invention include the following:

Diseases caused by Ascomycete fungi, such as Erysiphales as, for example, *Erysiphe cichoracearum* or *Uncinula necator*, and Dothideales as, for example, *Venturia inaequalis* or *Septoria tritici* (*Mycosphaerella graminicola*); or Diseases caused by Basidiomycete fungi, such as Uredinales as, for example, *Puccinia recondite*, Diseases caused by Oomycetes, such as Peronosporales as, for example, *Peronospora viticola*.

To illustrate the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

EXAMPLES

The test results described below demonstrate the enhancement in fungicidal efficacy and systemicity of the compounds of formula I by addition of the adjuvants (a), (b) or (c).

Biological Investigations

A Greenhouse Evaluations for Fungicidal Efficacy and Systemicity

Compound Handling Procedures

Formulated compounds are diluted using deionized water. Different formulations containing compound IA or IB are used in the greenhouse tests.

A1 Improvement in Curative Fungicidal Activity

TEST PROCEDURE: Curative plant disease control evaluation

DISEASE: Apple Scab

HOST: Apple, variety 'Morgenduft'

PATHOGEN: *Venturia inaequalis*

Apple seedlings are grown in pots in the greenhouse to the 4–8 leaf stage at which point they are inoculated by spraying with an aqueous suspension of conidia of *Venturia inaequalis*. Inoculated plants are kept in a moist chamber for two days, after which they are treated with the fungicide. During treatment, the plants rotate on a turntable in a spray cabin while being sprayed with three lateral nozzles. Dilutions of different formulations containing compound IA or IB are applied to apple plants. Treated plants are kept in the greenhouse with bottom watering until disease develops.

Disease as percent treated leaf area with disease is evaluated and then disease control calculated using the following formula:

$$\% \text{ disease control} = 100 - \frac{\% \text{ disease in treated plants}}{\% \text{ disease in untreated plants}} \times 100\%$$

The results of these evaluations are shown in Tables I, II and III:

TABLE I

Improvement in the curative fungicidal efficacy of Formulation B by Plurafac LF700

| Treatment | Dose (ppm)* | Disease Control Efficacy (%) |
|---|---|---|
| Formulation B | 50 | 62 |
| Formulation B | 10 | 14 |
| Formulation B | 2 | 0 |
| Formulation B + Plurafac LF700 | 50 + 1000 | 99 |
| Formulation B + Plurafac LF700 | 10 + 1000 | 78 |
| Formulation B + Plurafac LF700 | 2 + 1000 | 24 |
| Formulation B + Plurafac LF700 | 50 + 500 | 96 |
| Formulation B + Plurafac LF700 | 10 + 500 | 66 |
| Formulation B + Plurafac LF700 | 2 + 500 | 37 |
| Formulation B + Plurafac LF700 | 50 + 250 | 88 |
| Formulation B + Plurafac LF700 | 10 + 250 | 56 |
| Formulation B + Plurafac LF700 | 2 + 250 | 0 |

*1 ppm = 1 mg compound of formula I or adjuvant per 1 liter of spray mixture

TABLE II

Improvement in the curative fungicidal efficacy of Formulations E and G by Witconate AOK.

| Treatment | Dose (ppm) | Disease Control Efficacy (%) |
|---|---|---|
| Formulation E | 50 | 63 |
| Formulation E | 10 | 42 |
| Formulation E | 2 | 24 |
| Formulation G | 50 | 79 |
| Formulation G | 10 | 48 |
| Formulation G | 2 | 25 |
| Witconate AOK | 1000 | 11 |
| Formulation E + Witconate AOK | 50 + 1000 | 83 |
| Formulation E + Witconate AOK | 10 + 1000 | 58 |
| Formulation E + Witconate AOK | 2 + 1000 | 12 |
| Formulation F | 50 | 79 |
| Formulation F | 10 | 80 |
| Formulation F | 2 | 55 |
| Formulation G + Witconate AOK | 50 + 1000 | 100 |
| Formulation G + Witconate AOK | 10 + 1000 | 99 |
| Formulation G + Witconate AOK | 2 + 1000 | 79 |

Better performance of Formulation F (containing Witconate AOK) over Formulations E and G (not containing Witconate AOK) is apparent.

TABLE III

Improvement in the curative fungicial efficacy of Formulation I by different adjuvants

| Treatment | Dose (ppm) | Disease Control Efficacy (%) |
|---|---|---|
| Formulation I | 50 | 98 |
| Formulation I | 10 | 51 |
| Formulation I | 2 | 14 |
| Formulation I + Plurafac LF700 | 50 + 400 | 99 |
| Formulation I + Plurafac LF700 | 10 + 400 | 99 |
| Formulation I + Plurafac LF700 | 2 + 400 | 49 |
| Formulation I + Atplus MBA 1303 | 50 + 400 | 100 |
| Formulation I + Atplus MBA 1303 | 10 + 400 | 86 |
| Formulation I + Atplus MBA 1303 | 2 + 400 | 41 |
| Formulation I + Ukanil 2507 | 50 + 400 | 100 |
| Formulation I + Ukanil 2507 | 10 + 400 | 95 |
| Formulation I + Ukanil 2507 | 2 + 400 | 47 |
| Formulation I + Eumulgin CO 3522 | 50 + 400 | 100 |
| Formulation I + Eumulgin CO 3522 | 10 + 400 | 86 |
| Formulation I + Eumulgin CO 3522 | 2 + 400 | 24 |

A2 Improvement in Residual Fungicidal Activity

TEST PROCEDURE: Residual plant disease control evaluation

DISEASE: Grapevine Powdery Mildew

HOST: Grapevine, variety 'Müller-Thurgau'

PATHOGEN: *Uncinula necator*

Grapevine plants are raised from cuttings in pots in the greenhouse until they reach the 6–8 leaf stage.

Different formulations containing compound IA are applied to the grapevine plants by spraying the plants while they rotate on a turntable in a spray cabin with three lateral nozzles. Treated plants are returned to the greenhouse and bottom watered. Two days later the plants are inoculated by dusting them with conidia of *Uncinula necator*. Sporulating diseased leaves from stock culture plants are brushed with a brush in the air over the test plants so that the conidia can settle onto the upper leaf surfaces of the test plants.

Inoculated plants are kept in the greenhouse with bottom watering until disease develops.

Disease as percent treated leaf area with disease is evaluated and then disease control calculated using the following formula:

$$\% \text{ disease control} = 100 - \frac{\% \text{ disease in treated plants}}{\% \text{ disease in untreated plants}} \times 100\%$$

The results of this evaluation are shown in Table IV:

TABLE IV

Residual fungicidal efficacy improvement of Formulation G by Witconate AOK.

| Treatment | Dose (ppm) | Disease Control Efficacy (%) |
|---|---|---|
| Formulation G | 50 | 93 |
| Formulation G | 10 | 55 |
| Formulation G | 2 | 15 |
| Formulation G + Witconate AOK | 50 + 1000 | 100 |
| Formulation G + Witconate AOK | 10 + 1000 | 81 |
| Formulation G + Witconate AOK | 2 + 1000 | 60 |

A3 Improvement in Foliar Systemicity

TEST PROCEDURE: Foliar systemicity evaluation by bioassay

DISEASE: Cucumber Powdery Mildew

HOST: Cucumber, variety 'Bush Pickle'

PATHOGEN: *Erysiphe cichoracearum*

Cucumber seed (one/pot) is planted and maintained in the greenhouse for about 2 weeks until the primary leaf is fully expanded.

Formulated compounds are applied in a transverse band using an airbrush with a 0.5 mm circular nozzle at an air pressure of 500 mbar. The band is sprayed onto the lower leaf surface, perpendicular to the leaf axis using a cardboard mask with a 5-mm wide slit. The location of the band is marked on the upper leaf surface using a permanent marker and is typically 4 cm from the leaf tip.

After treated plants have dried, they are moved to the greenhouse and kept there for 2 days to allow for movement of the compounds. The plants are maintained with bottom watering.

Two days after application, the cucumber plants are inoculated by dusting them with powdery mildew conidia in the greenhouse. Sporulating diseased leaves from stock culture plants are brushed with a brush in the air over the test plants so that the conidia can settle onto the upper leaf surfaces of the test plants.

Evaluations are made 8–9 days after inoculation.

Compound movement is assessed by evaluating disease in different areas of each band-treated leaf. Distal movement and proximal movement: The distal and proximal disease-free zones on the upper leaf surface are measured in mm. The distal direction is from the band toward the leaf apex and the proximal direction is from the band toward the leaf base. The percent of the disease-free zone relative to the entire distance between the band and leaf apex or base is calculated (40 mm equals 100%).

Translaminar movement is assayed by evaluating the level of disease in the band area on the upper side of the leaf (opposite side from the treated lower leaf. Disease as percent leaf area with disease is evaluated and then disease control calculated using the following formula:

$$\% \text{ disease control} = 100 - \frac{\% \text{ disease in treated plants}}{\% \text{ disease in untreated plants}} \times 100\%$$

The results of these evaluations are shown in Table V:

TABLE V

Improvement of the Foliar Systemicity, both distal and translaminar, of Formulations B and C by Plurafac Surfactants and of Formulation G by Witconate AOK

| Treatment | Dose (ppm) | Distal Movement (mm from band) | Translaminar Movement Disease Control Efficacy (%) |
|---|---|---|---|
| Formulation B | 200 | 0 | 3 |
| Formulation C | 200 | 0 | 3 |
| Formulation G | 200 | 0 | 100 |
| Plurafac LF403 | 1000 | 0 | 0 |
| Plurafac LF700 | 1000 | 0 | 0 |
| Plurafac LF1300 | 1000 | 0 | 0 |
| Witconate AOK | 1000 | 0 | 7 |
| Formulation B + Plurafac LF403 | 200 + 1000 | 7 | 100 |
| Formulation B + Plurafac LF403 | 200 + 200 | 3 | 100 |
| Formulation B + Plurafac LF700 | 200 + 1000 | 8 | 100 |
| Formulation B + Plurafac LF700 | 200 + 200 | 7 | 100 |
| Formulation B + Plurafac LF1300 | 200 + 1000 | 9 | 100 |
| Formulation B + Plurafac LF1300 | 200 + 200 | 5 | 100 |
| Formulation C + Plurafac LF700 | 200 + 1000 | 7 | 100 |
| Formulation C + Plurafac LF700 | 200 + 600 | 5 | 100 |
| Formulation C + Plurafac LF700 | 200 + 200 | 4 | 100 |
| Formulation G + Witconate AOK | 200 + 1000 | 4 | 100 |
| Formulation G + Witconate AOK | 200 + 600 | 4 | 100 |
| Formulation G + Witconate AOK | 200 + 200 | 3 | 100 |

B Field Tests for Fungicidal Efficacy

B1 *Puccinia recondita* on Winter Wheat

| Crop | Winter wheat, variety 'Kanzler' |
|---|---|
| Plot size | 8 m² |
| Replicates | 3 |

The results of these field tests are shown in the following table VI:

TABLE VI

Rust control

| Treatment | Dose g ai/ha | % Rust control* Flag leaf |
|---|---|---|
| Untreated | | (8%) |
| Formulation H | 125 | 20 |
| Formulation H | 250 | 64 |
| Formulation B | 125 | 58 |
| Formulation B | 250 | 75 |
| Formulation H + Plurafac LF700 | 250 + 500 | 88 |
| Formulation B + Plurafac LF700 | 250 + 500 | 83 |
| Formulation B + Silwet ® L77 | 250 + 800 | 94 |

*Figures are % disease control relative to the infection level in the untreated (shown in brackets)

17

B2. *Septoria tritici* on Winter Wheat

| Crop | Winter wheat, variety 'Kanzler' |
|---|---|
| Plot size | 8 m² |
| Replicates | 3 |

The results of these field tests are shown in the following table VII:

TABLE VII

Septoria control

| Treatment | Dose g ai/ha | % Septoria control* Flag leaf |
|---|---|---|
| Untreated | | (8%) |
| Formulation H | 125 | 55 |
| Formulation H | 250 | 62 |
| Formulation B | 125 | 63 |
| Formulation B | 250 | 76 |
| Formulation H + Plurafac LF700 | 250 + 500 | 77 |
| Formulation B + Plurafac LF700 | 250 + 500 | 84 |
| Formulation B + Silwet ® L77 | 250 + 800 | 85 |

*Figures are % disease control relative to the infection level in the untreated (shown in brackets).

B3 *Septoria tritici* on Winter Wheat

| Crop | Winter wheat, variety 'Goupil' |
|---|---|
| Plot size | 6 m² |
| Replicates | 3 |

The results of these field tests are shown in the following table VIII:

TABLE VIII

Septoria control

| Treatment | Dose g.ai/ha | % Septoria control* Leaf 2 | % Septoria control* Flag leaf |
|---|---|---|---|
| Untreated | | (9%) | (90%) |
| Formulation H | 125 | 49 | 9 |
| Formulation H | 250 | 59 | 33 |
| Formulation B | 125 | 0 | 3 |
| Formulation B | 250 | 0 | 15 |
| Formulation H + Plurafac LF700 | 250 + 500 | 71 | 77 |
| Formulation B + Plurafac LF700 | 250 + 500 | 69 | 85 |
| Formulation B + Silwet ® L77 | 250 + 800 | 79 | 87 |

*Figures are % disease control relative to the infection level in the untreated (shown in brackets)

The above results clearly demonstrate that the adjuvants made an unexpectedly large improvement in the performance of the active ingredient. This increase in efficacy was particularly noteworthy on the variety Goupil (Table VIII) and continued late into the season also under severe disease pressure (90% infection in untreated). Even under this degree of disease pressure the mixture of the active ingredient plus adjuvant was able to demonstrate a performance equivalent to that of the best commercial standards. Such a performance against rust and, particularly, Septoria diseases was not previously seen, nor expected, from these dose rates.

18

Field trials have shown an improvement in performance from the use of adjuvants in a variety of crops (vines, apples, cereals).

What is claimed is:

1. A method for the enhancement of the activity and/or systemicity of fungicidal formulations applied to plants containing at least one triazolopyrimidine of formula I

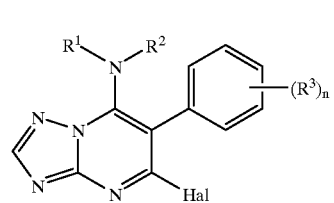

(I)

wherein $R^1$ and $R^2$ each independently represent hydrogen or an optionally substituted alkyl, alkenyl, alkynyl, alkadienyl, haloalkyl, aryl, heteroaryl, cycloalkyl, bicycloalkyl or heterocyclyl group, or $R^1$ and $R^2$, together with the adjacent nitrogen atom, represent an optionally substituted heterocyclic ring, $R^3$ represents a halogen atom or an alkyl or alkoxy group, n represents an integer from 0 to 5, and Hal represents a halogen atom, which comprises the addition of one or more consisting of non-ionic surface-active liquid polyalkoxylated aliphatic alcohols to the formulation or the tank mix, said polyalkoxylated aliphatic alcohol present in an amount sufficient to provide a ratio of the compound of formula I to polyalkoxylated aliphatic alcohol at 100:75 to 100:100,000 in the applied formulation.

2. A method according to claim 1 wherein said fungicidal formulation is provided in form of a suspension concentrate (SC) and said non-ionic surface-active liquid polyalkoxylated aliphatic alcohol is a straight-chained or branched aliphatic $C_{9-20}$ alcohol alkoxylated with 2 to 15 $C_{2-6}$alkoxy groups.

3. A method according to claim 1 wherein the polyalkoxylated aliphatic alcohol is a mixed ethoxylate/propoxylate.

4. A method according to claim 2 wherein the aliphatic $C_{9-20}$ alcohol alkoxylate is a mixed ethoxylate/propoxylate.

5. A method according to claim 1 wherein the ratio of fungicidal compound of formula I to the liquid polyalkoxylated aliphatic alcohol is from 100:125 to 1:500.

6. A fungicidal formulation for application to plants comprising at least one triazolopyrimidine of formula I

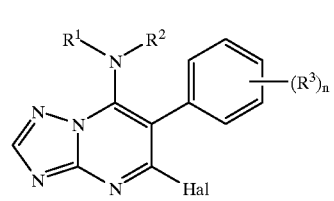

(I)

wherein $R^1$ and $R^2$ each independently represent hydrogen or an optionally substituted alky, alkenyl, alkynyl, alkadienyl, haloalkyl, aryl, heteroaryl, cycloalkyl, bicycloalkyl or heterocyclyl group, or $R^1$ and $R^2$, together with the adjacent nitrogen atom, represent an optionally substituted heterocyclic ring, $R^3$ represents a halogen atom or an alkyl or alkoxy group, n represents an integer from 0 to 5, and Hal represents a halogen atom, in which $R^1$ and $R^2$ each independently represent hydrogen or an optionally substituted alkyl, alkenyl, alkynyl, alkadienyl, haloalkyl, aryl, heteroaryl, cycloalkyl, bicycloalkyl or heterocyclyl group, or $R^1$ and $R^2$ together with the adjacent nitrogen atom represent an optionally substituted heterocyclic ring, $R^3$ represents a halogen atom or an alkyl or alkoxy group, n represents an integer from 0 to 5, and Hal represents a halogen atom, together with one or more non-ionic surface-active liquid polyalkoxylated aliphatic alcohols.

7. A formulation according to claim 6 which comprises an additional fungicidal compound.

8. A formulation according to claim 6 wherein the relative proportion of the triazolopyrimidine of formula I to liquid polyalkoxylated aliphatic alcohol is from 100–125 to 1:500.

9. A formulation according to claim 7 wherein the relative proportion of the triazolopyrimidine of formula I liquid polyalkoxyalated aliphtic alcohol in from 100–125 to 1:500.

10. A method for the control of phytopathogenic fungi on plants characterized by the use of an effective amount of a fungicidal compound of formula I,

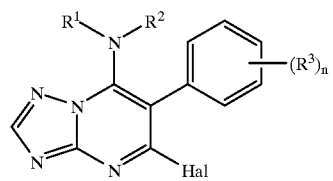

wherein
$R^1$ and $R^2$ each independently represent hydrogen or an optionally substituted alkyl, alkenyl, alkynyl, alkadienyl, haloalkyl, aryl, heteroaryl, cycloalkyl, bicycloalkyl or heterocyclyl group, or $R^1$ and $R^2$, together with the adjacent nitrogen atom, represent an optionally substituted heterocyclic ring, $R^3$ represents a halogen atom or an alkyl or alkoxy group, n represents an integer from 0 to 5, and Hal represents a halogen atom; in combination with one or more non-ionic surface-active liquid polyalkoxylated aliphatic alcohols.

11. A method according to claim 10 for the control of diseases caused by Ascomycete fungi.

12. A method according to claim 10 for the control of diseases caused by Dothidales or Erysiphales fungi.

13. A method according to claim 10 wherein the relative proportion of the triazolopyrimidine of formula I to liquid polyalkoxylated aliphatic alcohol is from 100:125 to 1:500.

* * * * *